United States Patent [19]
Taylor et al.

[11] Patent Number: 6,039,731
[45] Date of Patent: *Mar. 21, 2000

[54] APPARATUS AND METHOD FOR DETERMINING THE EXTENT OF ABLATION

[75] Inventors: Junius E. Taylor, Phoenix; Loren C. Acker, Tucson, both of Ariz.

[73] Assignee: Engineering & Research Associates, Inc., Tucson, Ariz.

[*] Notice: This patent is subject to a terminal disclaimer.

[21] Appl. No.: 09/182,712

[22] Filed: Oct. 29, 1998

Related U.S. Application Data

[63] Continuation of application No. 08/851,879, May 6, 1997, Pat. No. 5,868,737, which is a continuation-in-part of application No. 08/488,887, Jun. 9, 1995, Pat. No. 5,697,925
[60] Provisional application No. 60/016,647, May 15, 1996.

[51] Int. Cl.[7] .................................................. A61B 17/39
[52] U.S. Cl. ............................... 606/34; 606/38; 606/41; 600/374; 607/99
[58] Field of Search ............................... 600/374; 606/34, 606/38, 40, 41, 49; 607/99, 122

[56] References Cited

U.S. PATENT DOCUMENTS

| | | | |
|---|---|---|---|
| 4,641,649 | 2/1987 | Walinsky et al. | 128/303.1 |
| 4,785,815 | 11/1988 | Cohen | 128/642 |
| 4,869,248 | 9/1989 | Narula | 128/303.13 |
| 4,896,671 | 1/1990 | Cunningham et al. | 128/642 |
| 5,122,137 | 6/1992 | Lennox | 606/40 |
| 5,357,956 | 10/1994 | Nardella | 128/642 |
| 5,454,370 | 10/1995 | Avitall | 128/642 |
| 5,456,682 | 10/1995 | Edwards et al. | 606/31 |
| 5,462,545 | 10/1995 | Wang et al. | 606/41 |
| 5,697,925 | 12/1997 | Taylor | 606/34 |

OTHER PUBLICATIONS

"Basic Electrochemistry", Chapter 1.3, *Modern Electrochemistry*, John O'M. Bockris, published by Plenum Press., New York, dated 1970, pp. 12–31.

"Reversible Electrode Potentials", Chapter IV, *Electrochemistry Principles and Applications*, by Edmund C. Potter, published by Cleaver–Hume Press, Ltd., dated 1956, pp. 73–100.

"Electrodes and Electrochemical Cells", Chapter 4, *Introduction to Electrochemistry*, by D. Bryan Hibbert, published by MacMillan Press Ltd., dated 1993, pp. 58–89.

"Reversible Cells", Chapter XII, *Electrochemistry of Solutions*, by S. Glasstone, published by Methuen & Co. Ltd., London, dated 1937 (Second Edition), pp. 282–311.

Abst #22–"Tip Temperature is not and Indicator of Intramyocardial Temperatures During Radiofrequency Catheter Ablation", *Pacing and Clinical Electrophysiology*, NASPE Abstracts & Program, Apr. 1995, vol. 18, #4, Part II, p. 801.

Abst #145–"Radiofrequency Catheter Ablation Using A Saline Irrigated Electrode in Patients with Prior Failed Accessory Pathway Ablation", *Pacing and Clinical Electrophysiology*, NASPE, Apr. 1995, vol. 18, #4, Part II, p. 832.

"HeadsUp" brochure "EPT–1000 Cardiac Ablation System: The Ablation Technology You Need Today . . . ", EP Technologies Inc., Sunnyvale, California, dated Oct. 1994, (five pages).

(List continued on next page.)

*Primary Examiner*—Lee Cohen
*Attorney, Agent, or Firm*—Cahill, Sutton & Thomas, P.L.C.

[57] ABSTRACT

A catheter for use in an electrophysiological procedure to ablate a site includes a first electrode having a first work function and energized by a source of RF energy. A second electrode having a second work function is disposed adjacent tissue. The difference in work functions of the first and second electrodes, operating in the presence of an electrolyte represented by intermediate tissue, produces an exchange of electrical charges through chemical reaction to create a galvanic cell. The galvanic cell serves as a current source to provide a unique electrode signal used to regulate the RF energy applied to the first electrode.

8 Claims, 4 Drawing Sheets

OTHER PUBLICATIONS

"HeadsUp" brochure "ATKAR™: Radio Frequency Ablation SYstem", CardioRhythm, San Jose, California, dated Feb. 1995, (three pages).

Flyer "HAT 200 S: Radio Frequency System for Ablation, Recanalization and Angioplasty", Baylis Medical Company Inc., Montreal, Canada, (four pages).

"Surgical Treatment of Cardiac Arrhythmias", by Alden H. Harken, *Scientific American*, Jul. 1993, pp. 68–74.

"The Biophysics of Radiofrequency Catheter Ablation in the Heart: The Importance of Temperature Monitoring", by David E. Haines, PACE, vol. 16, Mar. 1993 (Part II), pp. 586–591.

"Basic Aspects of Radiofrequency Catheter Ablation", by Sunil Nath M.D. et al., *Journal of Cardiovascular Electrophysiology*, vol. 5, No. 10, Oct 1994, pp. 863–876.

"Biophysics and Pathology of Catheter Energy Delivery Systems", by Sunil Nath and David Haines, *Progress in Cardiovascular Diseases*, vol. XXXVII, No. 4, Jan./Feb. 1995, pp. 185–204.

"Physics and Engineering of Transcatheter Cardiac Tissue Ablation", by Boaz Avitall, M.D. et al., *JACC*, vol. 22, No. 3, Sep. 1993, pp. 921–932.

"Impedance Monitoring During Radiofrequency Catheter Ablation in Humans", by Mark Harvey et al., *PACE*, vol. 15, Jan. 1992, pp. 22–27.

"Assessment of Effects of a Radiofrequency Energy Field and Thermistor Location in an Electrode Catheter on the Accuracy of Temperature Measurement", by L. Blouin et al., *PACE*, vol. 14, May 1991, Part I, pp. 807–813.

"Simultaneous Multipolar Radiofrequency Ablation in the Monopolar Mode Increases Lesion Size", by Sean Mackey et al., *PACE*, Jun. 1995 (in press), pp. 1–15.

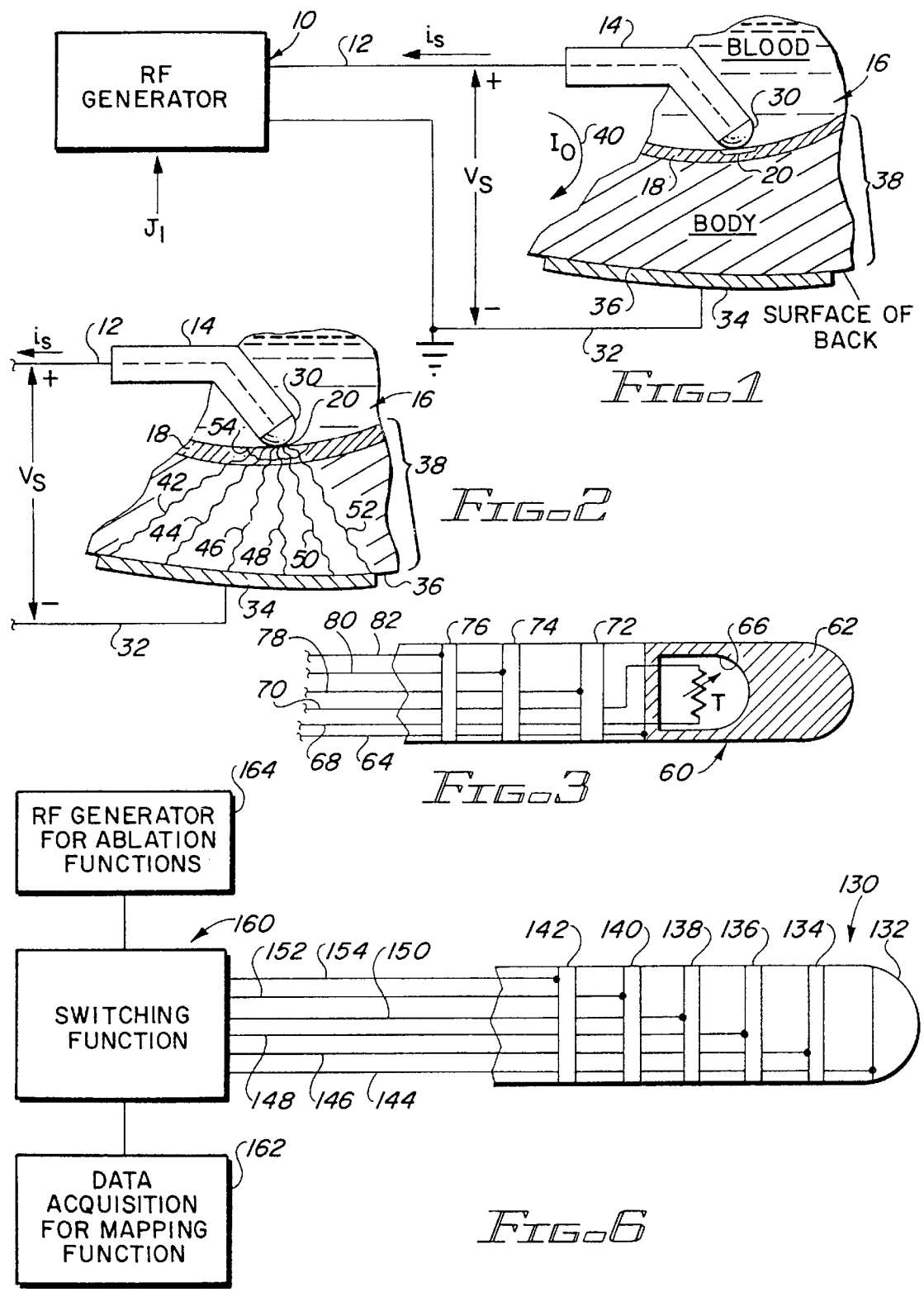

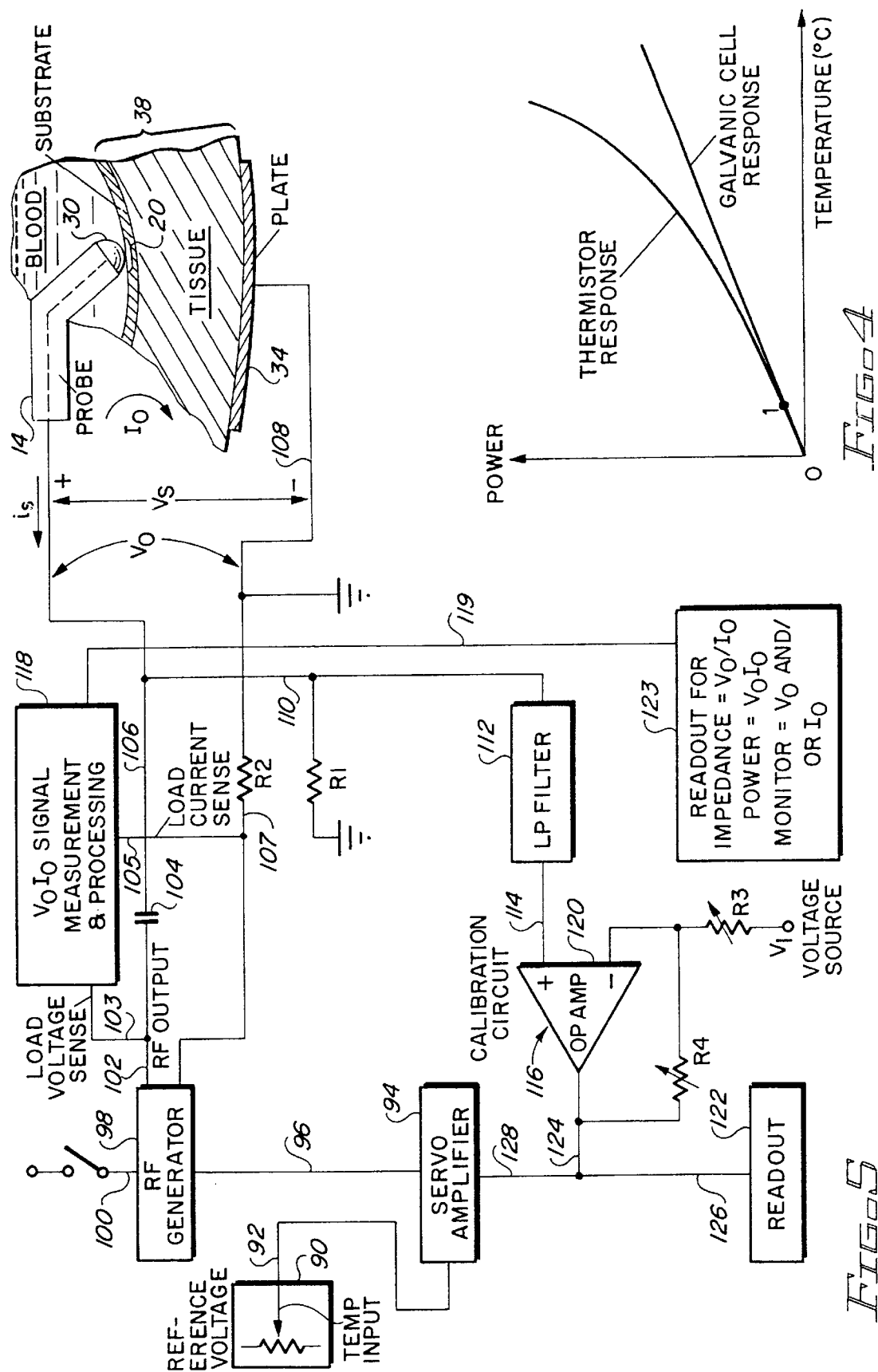

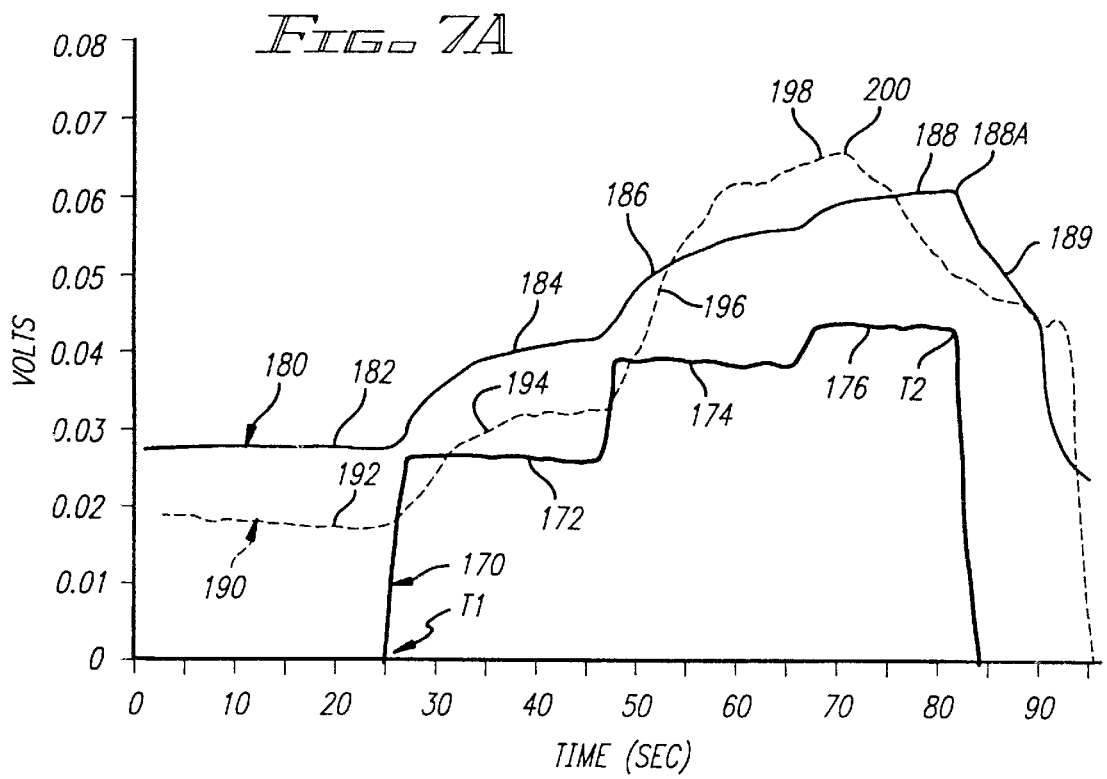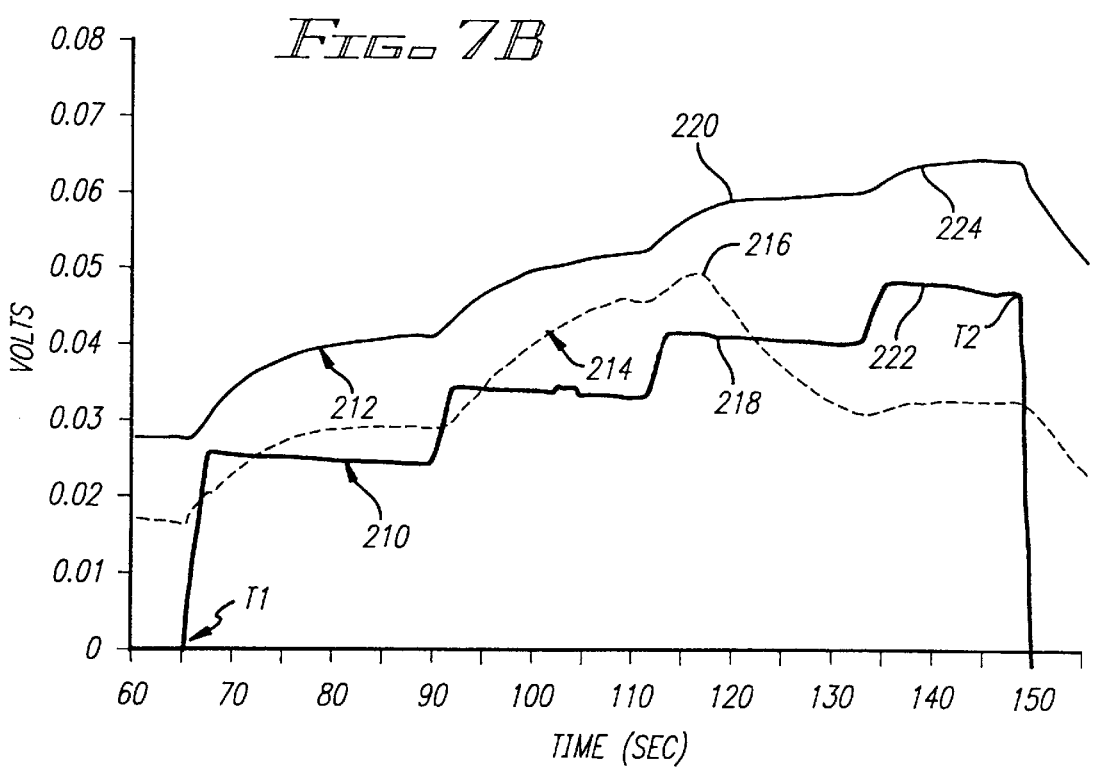

APPARATUS AND METHOD FOR DETERMINING THE EXTENT OF ABLATION

This is a continuation of application Ser. No. 08/851,879, filed May 6, 1997, now U.S. Pat. No. 5,868,737 entitled "APPARATUS AND METHOD FOR DETERMINING ABLATION", which is a continuation in part of application Ser. No. 08/488,887 filed Jun. 9, 1995, now U.S. Pat. No. 5,697,925, entitled "APPARATUS AND METHOD FOR THERMAL ABLATION" and the present application also claims priority with respect to common subject matter to provisional application Ser. No. 60/016,647 filed May 15, 1996, entitled "APPARATUS AND METHOD FOR INDICATING THERMAL ABLATION", all of which applications are assigned to the present Assignee and describe inventions by the present inventors.

BACKGROUND OF THE INVENTION

1. Field of the Invention

The present invention relates to catheters and, more particularly, temperature controlled catheter probes for ablating tissue.

2. Background of the Invention

The heart is a four chamber muscular organ (myocardium) that pumps blood through various conduits to and from all parts of the body. In order that the blood be moved in the cardiovascular system in an orderly manner, it is necessary that the heart muscles contract and relax in an orderly sequence and that the valves of the system open and close at proper times during the cycle. Specialized conduction pathways convey electrical impulses swiftly to the entire cardiac muscle. In response to the impulses, the muscle contracts first at the top of the heart and follows thereafter to the bottom of the heart. As contraction begins, oxygen depleted venous blood is squeezed out of the right atrium (one of two small upper chambers) and into the larger right ventricle below. The right ventricle ejects the blood into the pulmonary circulation, which resupplies oxygen and delivers the blood to the left side of the heart. In parallel with the events on the right side, the heart muscle pumps newly oxygenated blood from the left atrium into the left ventricle and from there out to the aorta which distributes the blood to every part of the body. The signals giving rise to these machinations emanates from a cluster of conduction tissue cells collectively known as the sinoatrial (SA) node. The sinoatrial node, located at the top of the atrium, establishes the tempo of the heartbeat. Hence, it is often referred to as the cardiac pacemaker. It sets the tempo simply because it issues impulses more frequently than do other cardiac regions. Although the sinoatrial node can respond to signals from outside the heart, it usually becomes active spontaneously. From the sinoatrial node impulses race to the atrioventricular (AV) node above the ventricles and speeds along the septum to the bottom of the heart and up along its sides. The impulses also migrate from conduction fibers across the overlying muscle from the endocardium to the epicardium to trigger contractions that force blood through the heart and into the arterial circulation. The spread of electricity through a healthy heart gives rise to the familiar electrocardiogram. Defective or diseased cells are electrically abnormal. That is, they may conduct impulses unusually slowly or fire when they would typically be silent. These diseased cells or areas might perturb smooth signalling by forming a reentrant circuit in the muscle. Such a circuit is a pathway of electrical conduction through which impulses can cycle repeatedly without dying out. The resulting impulses can provoke sustained ventricular tachycardia: excessively rapid pumping by the ventricles. Tachycardia dysrhythmia may impose substantial risk to a patient because a diseased heart cannot usually tolerate rapid rates for extensive periods. Such rapid rates may cause hypotension and heart failure. Where there is an underlying cardiac disease, tachycardia can degenerate into a more serious ventricular dysrhythmia, such as fibrillation. By eliminating a reentrant circuit or signal pathway contributing to tachycardia, the source of errant electrical impulses will be eliminated. Ablation of the site attendant such a pathway will eliminate the source of errant impulses and the resulting arrhythmia. Mapping techniques for locating each of such sites that may be present are well known and are presently used.

Interruption of the errant electrical impulses is generally achieved by ablating the appropriate site. Such ablation has been performed by lasers. The most common technique used at an ablation site involves the use of a probe energized by radio frequency radiation (RF). Measurement and control of the applied RF energy is through a thermistor (or it could be a thermocouple) located proximate the RF element at the tip of a catheter probe. While such a thermistor may be sufficiently accurate to reflect the temperature of the thermistor, it is inherently inaccurate in determining the temperature of the tissue at the ablation site. This results from several causes. First, there is a temperature loss across the interface between the ablation site (usually variable due to position of electrode) and the surface of the RF tip. Second, the flow of blood about the non-tissue contact portion of the conductive RF tip draws off heat from the ablation site which causes the thermistor to be cooler than the tissue under ablation. However, temperatures above 100° C. causes coagulum formation on the RF tip, a rapid rise in electrical impedance of the RF tip, and excessive damage to the endocardium. Third, there is a lag in thermal conduction between the RF tip and the thermistor, which lag is a function of materials, distance, and temperature differential. Each of these variables may change constantly during an ablation procedure.

To ensure that the ablation site tissue is subjected to heat sufficient to raise its temperature to perform irreversible tissue damage, the power transmitted to the RF tip must be increased significantly greater than that desired for the ablation in view of the variable losses. Due to the errors of the catheter/thermistor temperature sensing systems, there is a propensity to overheat the ablation site tissue needlessly. This creates three potentially injurious conditions. First, the RF tip may become coagulated. Second, tissue at the ablation site may "stick to" the RF tip and result in tearing of the tissue upon removal of the probe. This condition is particularly dangerous when the ablation site is on a thin wall of tissue. Third, inadequate tissue temperature control can result in unnecessary injury to the heart including immediate or subsequent perforation.

When radio frequency current is conducted through tissue, as might occur during a procedure of ablating a tissue site on the interior wall (endocardium) of the heart with a radio frequency energized catheter, heating occurs preliminarily at the myocardial tissue interface with the tip of the catheter. Given a fixed power level and geometry of the catheter probe, the temperature gradient from the probe interface and a distance, r, into the tissue is proportional to $1/r^4$. Heating is caused by the resistive (OHMIC) property of the myocardial tissue and it is directly proportional to the current density. As may be expected, the highest temperature occurs at the ablation site which is at the interface of the RF tip and the tissue.

When the temperature of the tissue at the ablation site approaches 100° C., a deposit is formed on the RF tip that will restrict the electrical conducting surface of the RF tip. The input impedance to the RF tip will increase. Were the power level maintained constant, the interface current density would increase and eventually carbonization would occur. At these relatively extreme temperatures, the RF tip will often stick to the surface of the tissue and may tear the tissue when the RF tip is removed from the ablation site.

To effect ablation, or render the tissue nonviable, the tissue temperature must exceed 50° C. If the parameters of the RF tip of a catheter are held constant, the size and depth of the lesion caused by the ablation is directly proportional to the temperature and time at the interface (assuming a time constant sufficient for thermal equilibrium). In order to produce lesions of greatest depth without overheating the tissues at the interface, critical temperature measurement techniques of the RF tip are required.

The current technology for measuring the temperature of an RF tip embodies a miniature thermistor(s) located in the RF tip of the probe. The present state of the art provides inadequate compensation for the thermal resistance that exists between the thermistor and the outer surface of the RF tip, which may be in variable contact with the tissue and affected by blood cooling or between the outer surface of the RF tip and the surface of the adjacent tissue. Because of these uncertainties contributing to a determination of the specific temperature of the tissue at the interface, apparatus for accurately determining when ablation actually occurs would be of great advantage in performing an electrophysiological procedure to ablate a specific site(s) of the myocardial tissue.

SUMMARY OF THE INVENTION

A catheter probe having a metal tip energized by an RF generator radiates RF energy as a function of the RF energy applied. When the tip is placed adjacent tissue at an ablation site, the irradiating RF energy heats the tissue due to the ohmically resistive property of the tissue. The catheter tip placed adjacent the ablation site on tissue in combination with an electrically conducting dissimilar metal plate in contact with tissue at a location remote from the ablation site and an electrolyte defined by the intervening tissue create a galvanic cell when the tip and plate have different work functions because of migration of electrical charges therebetween. By loading the galvanic cell, the DC output current is a linear function of the temperature of the ablation site heated by the RF energy. The DC output current of the galvanic cell is used to regulate the output of the RF generator applied to the catheter tip to control the current density at the ablation site. When ablation at the ablation site occurs, the value of the DC output signal drops dramatically irrespective of further applied RF energy and provides a signal to terminate application of further RF energy to avoid possible coagulation of the RF tip, sticking of the tissue to the RF tip and perforation of the tissue.

It is therefore a primary object of the present invention to provide a signal for indicating occurrence of tissue damage at an ablation site in response to RF energy radiated from a catheter tip during an ablation procedure.

Another object of the present invention is to provide an output signal representative of the occurrence of tissue damage at an ablation site for subsequently regulating the RF radiation power level of a probe performing the ablation procedure to obtain tissue damage to a desired depth.

Yet another object of the present invention is to generate a signal representative of actual tissue damage at an ablation site in order to cease further heating of the ablation site by regulating the radiation of RF energy from an ablating RF tip.

Still another object of the present invention is to provide apparatus for determining the occurrence of tissue damage of a cardiac impulse pathway and thereafter cease further heating of the ablation site.

A further object of the present invention is to provide a self-regulating catheter mounted RF radiating element controlled by an output signal reflective of actual tissue damage at an ablation site on the endocardium of a heart suffering tachycardia dysrhythmia and destroy a pathway of errant electrical impulses at least partly contributing to the tachycardia dysrhythmia.

A still further object of the present invention is to provide a method for controlling heating and sensing the occurrence of actual tissue damage at an ablation site and thereafter terminating further heating of the ablation site when the desired depth of tissue damage has been achieved.

These and other objects of the present invention will become apparent to those skilled in the art as the description thereof proceeds.

BRIEF DESCRIPTION OF THE DRAWINGS

The present invention may be described with greater specificity and clarity with reference to the following drawings, in which:

FIG. 1 illustrates a simplified representation of the present invention;

FIG. 2 illustrates the current density at an ablation site during an ablation procedure;

FIG. 3 illustrates a representation of a catheter probe embodying a thermistor useful in the present invention;

FIG. 4 illustrates representatives curves for calibrating the temperature of an ablation site through use of a probe embodying a thermistor;

FIG. 5 is a block diagram of circuitry representatively shown in FIG. 1;

FIG. 6 illustrates a catheter probe for sequentially mapping the endocardium, identifying a site to be ablated and ablating the site without relocating the probe;

FIGS. 7A and 7B are graphs illustrating the respective output signals of the power level applied by a catheter tip, the temperature sensed by a catheter mounted thermistor and the galvanic current at an ablation site during an ablation procedure.

DETAILED DESCRIPTION OF THE PREFERRED EMBODIMENT

Figure 8:
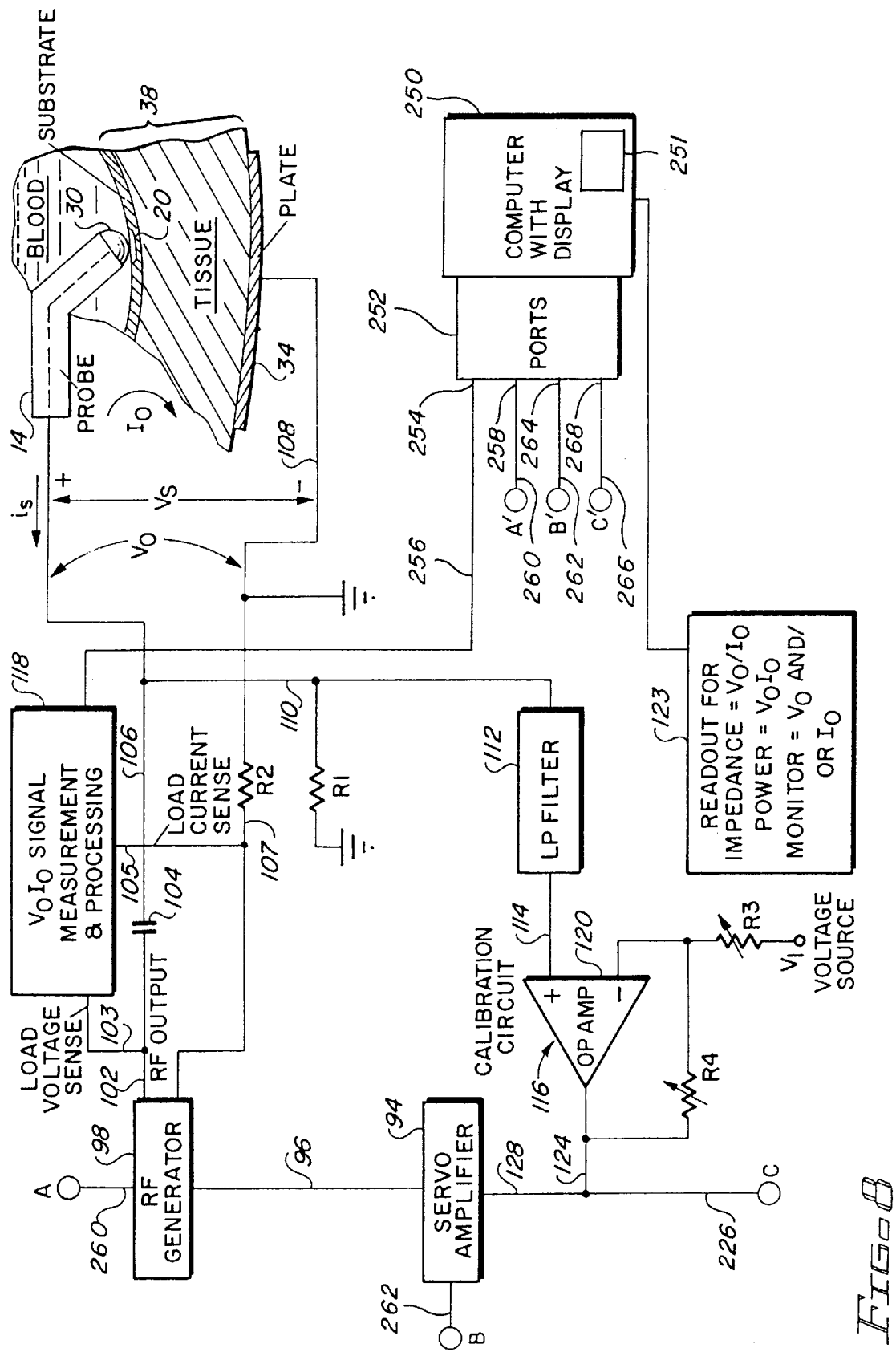
FIG. 8 illustrates the use of a computer to perform certain of the functions manually performed with the circuitry shown in FIG. 5 and to provide displays of information.

Two electrodes of different metals having different work functions in the presence of an electrolyte (such as blood) a saline solution or living tissue, will produce an exchange of electrical charges and an electromotive force (emf) is generated. This emf generator is known as a galvanic cell. A technical discussion of the history of galvanic cells is set forth in Chapter 1.3, entitled "Basic Electrochemistry" (pages 12–31) in a textbook entitled *Modern Electrochemistry*, authored by John O'M. Bockris, published by Plenum Press., New York, dated 1970. Detailed technical discussions of galvanic cells can be found in: Chapter 4, entitled "Reversible Electrode Potentials" (pages 73–100) of a textbook entitled *Electrochemistry Principles and Applications*, authored by Edmund C. Potter, published by Cleaver-Hume Press, Ltd., dated 1956; Chapter 4 entitled "Electrodes and Electrochemical Cells" (pages 59–89) of a textbook entitled *Introduction to Electrochemistry*, authored by D. Bryan Hibbert, published by MacMillan Press Ltd., dated 1993; and Chapter 12 entitled "Reversible Cells" (pages 282–311) of a textbook entitled *Electrochemistry of Solutions*, authored by S. Glasstone, published by Methuen & Co. Ltd., London, dated 1937 (Second Edition). These technical discussions are incorporated herein by reference.

The magnitude of the potential of a galvanic cell is a function of the electrolyte concentrates and the metals' work functions. The open circuit voltage of the galvanic cell is essentially constant despite temperature changes at the interface between the electrodes and the electrolyte. However, by loading the galvanic cell with a fixed value shunt resistance it simulates a current generator which has an output signal directly proportional to the temperature of the metal and electrolyte interface. The output signal of the current generator can be calibrated as a function of the temperature at the interface. A simple method for calibration is that of referencing the output of the current generator with the output of a thermistor embedded in the electrode at steady state power and temperature conditions at an initial or first temperature and at a second temperature. This will provide two data points for the power/temperature curve of the current generator. Since the output of the current generator is linear, the curve can be extended to include all temperatures of interest.

The present invention is directed to apparatus for ablating an errant cardiac conduction pathway responsible for or contributing to arrhythmia of the heart. The ablation process is performed by heating the ablation site tissue to a temperature typically exceeding 50° C., sufficient to cause ablation of the cells contributing to the errant impulse pathway. The ablation is effected by irradiating the ablation site tissue with radio frequency (RF) energy. For this purpose, a catheter probe tip is positioned adjacent the ablation site, which site has been previously determined by mapping procedures well known to physicians and those skilled in the art. Upon positioning of the probe tip at the ablation site, a source of RF energy is actuated to transmit RF energy through a conductor to the tip of the probe. The RF energy radiates from the tip into the ablation site tissue. The current density at the ablation site is a function of the power of the RF energy irradiating the ablation site and the surface area defining the interface between the tip and the ablation site tissue. Control of the tissue temperature at the interface is of significant importance to control the area and depth of ablation in order to perform the degree of ablation necessary, to prevent coagulation on the tip, to prevent the tip from sticking to the tissue, to prevent avoidable injury to adjacent tissue, to prevent perforation of the tissue, and to avoid unnecessary heating of the blood flowing in and about the tip.

Catheter probes having a thermistor embedded at the tip have been used to perform an ablation procedure and the amount of RF energy applied has been regulated as a function of the temperature sensed by the thermistor. Such temperature sensing is inherently inaccurate in determining the temperature at the ablation site due to the numerous variables present. First, there exists a temperature loss through the interface between the ablation site and the surface area of the tip in contact with tissue. Second, there exists a thermal resistance within the tip which causes temperature lag between the surface area of the tip in contact with the ablation site and the thermistor. Third, the orientation of the tip with respect to the ablation site will vary with a consequent variation of heating of the ablation site. Finally, the blood flowing about the tip area not in tissue contact will draw off heat as a function of both flow rate and orientation of the tip with respect thereto. By experiment, it has been learned that the differences between the tissue temperature at the ablation site and the temperature registered by a thermistor may range from 10° C. to 35° C. Such temperature excursion may result in unnecessary injury without a physician being aware of the injury caused at the time of the ablation procedure. Where ablation is being performed upon a thin wall myocardium, a puncture or a perforation at a later time can and does occur with potentially disastrous results.

The present invention is shown in simplified format in FIG. 1. An RF generator 10 serves as a source of RF energy. The output of the RF generator is controlled by an input signal identified as $J_1$. The RF energy, as controlled by $J_1$, is transmitted through a conductor 12 to a catheter probe 14. This probe is depicted as being lodged within a blood filled chamber 16 of a heart. The chamber may be the right or left atrium or the right or left ventricle. Probe 14 is lodged adjacent, for instance, tissue 18 at an ablation site 20 representing a reentrant circuit to be ablated. As represented, blood continually flows through chamber 16 about and around probe 14.

Probe 14 includes a tip 30 electrically connected to conductor 12 to irradiate ablation site 20 with RF energy.

Typically, the frequency may be in the range of about 350 kHz to about 1200 kHz. Such irradiation of the ablation site will result in heating of the ablation site as a function of the current density at the ablation site. The current density is determined by the energy level of the irradiating RF energy and the surface area of the ablation site. More specifically, the heat generated is proportional to the current density squared. This may be expressed as: $T(r)=kPd=kI^2R=(J_O^2/r^4)R$, where T=temperature, r=distance from the interface, $J_O$=current density at the interface, Pd=power dissipated, I=current at the interface, and R=resistance at the interface. The return path to RF generator 10 is represented by conductor 32. Conductor 32 is electrically connected to a relatively large sized plate 34 placed adjacent the patient's skin, preferably a large surface area of the patient's back. To ensure good electrical contact, an electrically conducting salve may be disposed intermediate plate 34 and patient's back 36. The fluid and tissues of the patient intermediate tip 30 and plate 34, represented by numeral 38, constitutes, in combination, an electrolyte and therefore an electrically conductive path between the tip and the plate. The DC current flow is represented by $i_s$ and the DC voltage is represented by $v_S$.

As more particularly illustrated in FIG. 2, ablation site 20 has a relatively high concentration of current paths, representatively depicted by diverging lines identified with numerals 42, 44, 46, 48, 50, and 52. These current paths are in close proximity with one another at the ablation site. The resulting high current density will produce heating of the ablation site as a function of the current density. The depth of the ablated tissue is representatively illustrated by line 54. The current density proximate back 36 of the patient adjacent plate 34 is relatively low. With such low current density, essentially no heating of the skin adjacent plate 34 will occur. It is to be appreciated that FIG. 2 is not drawn to scale and is intended to be solely representative of relative current densities resulting from irradiation of an ablation site by tip 30.

Ablation with tissue temperature control permits the physician to optimize the ablation process by allowing the ablation to occur at maximum temperature that is below a temperature conducive to formation of coagulation on the tip. Since such temperature is a function of the RF energy irradiating the ablation site tissue, control of the amount of RF energy transmitted via conductor 12 to the tip is necessary. A presently available type of catheter probe 60 is illustrated in FIG. 3. This probe includes a tip 62 for radiating RF energy received through conductor 64 from a source of RF energy. A thermistor 66 is embedded in tip 62 or in sufficient proximity with the tip to be responsive to the temperature of the tip. A pair of conductors 68 and 70 interconnect thermistor 66 with a signal detection circuit to provide an output signal representative of the temperature sensed. Furthermore, probe 60 may include mapping electrodes 72, 74 and 76. These electrodes may be used in conjunction with manipulation of probe 60 within the heart to detect and identify errant impulse pathways causing cardiac arrhythmia. Conductors 78, 80 and 82 connect electrodes 72, 74 and 76, respectively, to circuitry associated with the mapping functions, as is well known.

As stated above, thermistor 66 is incapable of providing an accurate representation of the temperature at the ablation site. In summary, the causes contributing to inaccurate temperature representation are heat loss through the interface between tip 30 and ablation site 20 (see FIG. 2), thermal lag between the area of tissue in contact with the tip and the sensing element of the thermistor, and heat loss resulting from flow of blood about the tip area not in contact with the tissue.

By experimentation, it has been learned that the combination of tip 30, plate 34 and body 38 perform in the manner of a galvanic cell provided that the tip and the plate are metallic and of different work functions since body 38 acts as an electrolyte; the body is permeated by fluids having electrical properties similar to a saline solution. Experiments indicate that a preferable material for tip 30 is platinum and a preferable material for plate 34 is copper. The open circuit voltage ($v_S$) of this galvanic cell is essentially independent of the temperature of ablation site 20. However, if the galvanic cell is heavily loaded with a shunt resistor, the galvanic cell serves as a current source and the magnitude of the current ($i_S$) is linear as a function of the tissue temperature at the ablation site through the 37° C. to 100° C. temperature range of interest. The temperature of the tissue adjacent plate 34 is the body temperature since the current density is insufficient to generate heat of any consequence. Thus, the galvanic cell created by the apparatus illustrated in FIG. 2 provides an output signal representative of the tissue temperature at ablation site 20 and irrespective of the temperature of tip 30.

One method for calibrating the galvanic cell will be described, but other methods may be used which do not require the presence of a thermistor at the tip. A thermistor is embedded in the tip of a catheter probe, such as probe 60. For reasons set forth above, the output of the thermistor is inherently inaccurate with respect to the actual tissue temperature at the ablation site; moreover, the temperature sensed by the thermistor as a function of the power applied is generally nonlinear. However, within a temperature range from a quiescent standby state to a small temperature increase at the ablation site (small increase in power applied), the output signal of the thermistor is essentially linear. By matching the output curve of the thermistor with the generally linear response curve of the galvanic cell, two coincident reference points can be determined. Referring to FIG. 4, there is illustrated a thermistor response curve and a galvanic cell response curve manipulated to be coincident from a point 0 to a point 1. By correlating the temperature indication of the thermistor at these two points, with the current output ($i_S$) of the galvanic cell, the temperature response can be linearly extrapolated to obtain a temperature reading correlated with the current output of the galvanic cell. That is, for any given current output of the galvanic cell, the tissue temperature of the ablation site can be determined. Thus, if probe 14 illustrated in FIGS. 1 and 2 is of the type shown in FIG. 3, calibration of the probe at the ablation site can be readily determined. Other methods for calibrating the current output with temperature can also be employed, as set forth above.

Referring to FIG. 5, there is illustrated a block diagram of the major components necessary to control the power applied to a catheter probe for ablating an errant impulse pathway at an ablation site. FIG. 5 shows a temperature input circuit 90 for setting a reference voltage equivalent to the tissue temperature sought for an ablation site at which an ablation procedure is to be performed. The resulting output signal is transmitted through conductor 92 to a servo amplifier 94. The servo amplifier provides an output signal on conductor 96 to control the output power of RF generator 98. A switch 100 controls operation of the RF generator. The RF energy output is impressed upon conductor 102. A blocking capacitor 104 is representative of a high pass filter and blocks any DC component of the signal on conductor 102. Conductor 106 interconnects the blocking capacitor with tip 30 of probe 14 and transmits RF energy to the tip. Tip 30 irradiates ablation site 20 of an endocardium, wall, membrane, or other living tissue to be irradiated with RF energy. Tip 30 is of a substance, such as platinum or other metal, having a first work function. Plate 34 displaced from tip 30, is of a substance, such as copper or other metal, having a second work function which is different from the first work function. Plate 34 is in electrical contact with a mass of tissue 38 intermediate tip 30 and the plate. This tissue, being essentially a liquid and having electrical characteristics of a saline solution, serves in the manner of an electrolyte interconnecting tip 30 and plate 34. The resulting galvanic cell formed, as discussed above, provides a DC output voltage $v_S$ across conductors 106 and 108. Shunt impedance R1 heavily loads the galvanic cell formed to convert the galvanic cell to a current source ($i_S$) to provide an output signal reflective of the tissue temperature at ablation site 20. The output signal from the galvanic cell is transmitted through conductor 110 to a lowpass filter 112. The output of the lowpass filter is conveyed via conductor 114 to an operational amplifier 120 of a calibration circuit 116. Additionally, a signal measurement and processing circuit 118, connected to conductor 102 through conductor 103 to provide sampling of the output load voltage ($V_O$). It is also connected to conductor 107 through conductor 105 to provide an input signal of the load output) current ($I_O$) sensed, processes the input signals to 0provide an indication of the impedance, power, and voltage and current levels. A readout 123, connected through conductor 119 to signal measurement and processing circuit 118, provides each of a plurality of indications of impedance, power, voltage level, current level, etc.

Variable resistors R3 and R4, in combination with operational amplifier 120, are representative of adjustments to be made to correlate the output current ($i_S$) of the galvanic cell with the tissue temperature of ablation site 20. Calibration circuit 116 can perform the above-described correlation of the thermistor indicated temperature with the current output signal of the galvanic cell to obtain a tissue temperature indication of the ablation site as a function of the current ($i_S$)

generated by the galvanic cell. A readout 122, connected via conductors 124,126 with the calibration circuit, may be employed to provide an indication of the tissue temperature of the ablation site. An output signal from the calibration circuit is also conveyed via conductors 124 and 128 to servo amplifier 94. This output signal is reflective of the tissue temperature at the ablation site. Thereby, the servo amplifier receives an input signal reflective of the tissue temperature at the ablation site. Circuitry of servo amplifier 94 will determine whether to raise or lower the tissue temperature of the ablation site or to maintain it at its preset temperature. A command signal to increase, to decrease, or to maintain the power output of the RF generator is transmitted from servo amplifier 94 through conductor 96 to the RF generator.

Referring to FIG. 6, there is illustrated a variant of probe 14 useable with the present invention. The combination of first mapping a site of interest and then ablating the site is a lengthy procedure. Were it possible to ablate a site identified during a mapping procedure without relocating the probe or without replacing the mapping probe with an ablating probe, significant time would be saved. FIG. 6 illustrates a catheter probe 130, which may be sufficiently flexible to position all or some of its length in contacting relationship with the surface of the myocardial tissue to be mapped. A tip 132, which may be similar to tip 30 of probe 14, is disposed at the distal end. A plurality of mapping electrodes, such as rings 134, 136, 138, 140 and 142 are disposed proximally along the probe from tip 132. These rings serve a function of mapping the tissue of interest to identify and locate a site to be ablated to destroy the circuit responsible for errant impulses. For these rings to work in the manner of tip 30, as described with reference to FIGS. 1–5, the rings are preferably metallic and have a work function different from that of plate (or electrode) 34. One of a plurality of conductors 144, 146, 148, 150, 152 and 154 interconnect the respective tip and rings with the output of a switching circuit(s) 160. A data acquisition circuit 162 is selectively interconnected through switching circuit 160 to each of rings 132–142 and possibly tip 132. The data acquisition circuit collects data sensed by the rings and/or tips to map the tissue surface traversed by the probe. Upon detection of a site to be ablated to destroy an impulse pathway (circuit), switch circuit 160 switches to interconnect the respective ring (or tip) with RF generator 164. Upon such interconnection, the respective ring (or tip) will irradiate the identified site with RF energy and the ablation function, as described above along with the tissue temperature control function, will be performed.

From this description, it is evident that upon detection of a site located by performing a mapping function, ablation of the site can be performed immediately without further movement or manipulation of the catheter probe. Furthermore, the ablation function can be performed with the circuitry illustrated in FIG. 5 to heat and maintain the tissue at a predetermined temperature until ablation is completed.

Empirically, it has been determined that the circuit and apparatus for ablating tissue, as illustrated in FIG. 5, provides to a physician a very accurate indication of the tissue temperature at the ablation site. With such accuracy, ablation procedures are capable of being performed on thin wall tissue without fear of coagulation of the tip, adhesion of tissue to the tip or puncture, which fears exist with presently used ablation performing apparatus. Furthermore, accurate representation of the temperature at the ablation site is no longer critically dependent upon the orientation of the probe at the ablation site nor upon the extent of the depression of the tissue in response to the pressure exerted by the probe tip. Because of these very difficult to control variables, complete ablation of the errant impulse pathway was not always achieved if the physician were overly cautious. Tip coagulation, sticking tissue and sometimes excessive injury to and puncture of the tissue occurred if the physician were more aggressive. These results were primarily due to the inaccuracy of the information conveyed to the physician during the procedure and not so much due to poor technique.

As will become evident from the above description, tip 30 (and tip 132) does not need a thermistor or a thermocouple to set or determine the temperature of the ablation site. Therefore, the probe can be smaller and more versatile than existing probes. Moreover, the probe can be manufactured at a substantially reduced cost because it is more simple than existing devices.

Rings (or other electrodes) located on the catheter can be used for mapping sites of errant impulses and any of the rings (or other electrodes) can be used to irradiate the tissue at such site after identification of the site and without repositioning of the catheter.

As a result of in vivo testing on canines in conjunction with more accurate and expanded signal displays, a further important capability of the present invention has been uncovered. Referring to FIG. 7A, there is illustrated a graph of three signals present during an ablation procedure. The ordinate of the graph depicts time in seconds and the abscissa depicts voltage. Curve 170 depicts the RF power level applied to catheter tip 30 and the voltage scale is proportional to the power level. The power applied is shown as steps 172, 174 and 176. The power is maintained essentially constant at each of these power levels. The power is turned on at time $T_1$ and turned off at time $T_2$. Curve 180 depicts the output of the thermistor within tip 30 (such as thermistor 66 within tip 60 shown in FIG. 3) and the voltage scale is proportional to the temperature sensed by the thermistor. Prior to time $T_1$, section 182 of curve 180 is essentially quiescent and representative of an essentially constant temperature. Upon application of power, the temperature recorded by the thermistor increases, as depicted by section 184, which increase is essentially correlated with the time of power level 172. Upon further increase of the power level (174) section 186 depicts a higher temperature. Similarly, upon application of power level 176, section 188 depicts a yet higher temperature level. After termination of the power applied at time $T_2$, the temperature of the thermistor drops, as depicted by section 189.

The current ($I_O$) generated by the galvanic cell is represented by curve 190 and the voltage scale is proportional to the current. Prior to time $T_1$, the current is essentially constant, as depicted by segment 192. At time $T_1$ and upon application of RF power, the current increases, as depicted by segment 194, until a quiescent state is established after an initial duration of applied power corresponding with power level 172. Upon an increase of applied power level 174, the current increases sharply in segment 196. During the latter time period of power level 174, the rate of increase of current during segment 196 decreases. Upon application of additional power, represented by power level 176, the rate of increase of current level depicted by segment 198 remains essentially constant to a peak identified by numeral 200. It is to be noted that this peak occurs after power corresponding with power level 176 has been applied for a short duration. Thereafter, the current steadily decreases (decays). It may be noted that the peak of the curve representing the temperature of the thermistor, and depicted by point 188A, occurred significantly later than the peaking of curve 190 at point 200.

The cause for peaking of the current produced by the galvanic cell during application of a constant power level was not immediately understood nor evident from the data. Upon further inspection of an in vivo ablation site in the heart of a canine, it was learned that peaking occurred simultaneously with tissue damage (discoloration) at the interface between the catheter tip and the tissue. It is believed that the tissue damage resulted in a change in ion and cation distribution, or change in charge distribution, at the ablation site. That is, the resulting environment of damaged tissue having a reduced charge distribution significantly affected the current generated by the galvanic cell and provided a clear and unambiguous signal.

From these results, one can then draw the following conclusions. First, and as set forth above, the output current of the galvanic cell is correlatable as a function of the temperature of an ablation site irradiated with RF energy. Second, the current output of the galvanic cell formed by the subject undergoing an ablation procedure provides an unambiguous and readily apparent indication (signal) of when the tissue sought to be ablated at an ablation site has in fact been ablated. Third, upon detection of peak 200 during an ablation procedure, further application of RF power may be terminated. Since ablation generally requires a temperature in the range of about 50 to 55 degrees Centigrade, conditions giving rise to tip coagulation, sticking tissue and perforation of the tissue will not occur. The resulting safety feature of the ablation procedure and the elimination of serious possibility for consequential injury will be achieved to a degree never before available.

Referring to FIG. 7B, there is representatively shown a curve 210 depicting applied RF power levels, curve 212 depicting the temperature of a thermistor disposed in a catheter tip performing an ablation procedure, and curve 214 depicting the current output of a galvanic cell which would be present during an ablation procedure. Curve 214 depicts a peak 216 occurring during application of power corresponding with power level 218. At this power level, segment 220 of curve 212 has an initial rise followed by a reduced rate of rise of temperature. Despite the constantly applied power level, curve 214 decreases subsequent to peak 216. Upon application of a higher power level, represented by numeral 220, the decrease of curve 214 is halted and after a small rise maintains an essentially quiescent state. However, segment 224 of curve 212 increases abruptly with a following reduced rate of increase. Upon termination of power at $T_2$ curves 214 and 212 decrease.

The curves depicted in FIG. 7B clearly show that peak 216 occurring in curve 214 is unaffected by subsequent applications of increased power and despite such increased power provides an unambiguous indication of ablation of the tissue at an ablation site.

It is presently believed that the degree of decay of the current signal (curve 180 or 214) is a function of the tissue damage. Moreover, it is believed that the depth of ablation can be controlled as a function of power level and time subsequent to occurrence of ablation (peak 200 or 216).

Referring to FIG. 8, there is illustrated an improved version of the apparatus shown in FIG. 5. The improved version includes a computer 250 which includes a visually perceivable display screen 251 for depicting data, two-dimensional images, etc. For example, readout 123 (depicted in FIG. 5) may be one of the group of images that would be displayed by computer 250. The computer may include a plurality of ports, represented by block 252, through which data, whether digital or analog, may be inputted and outputted. Load/impedance measurement circuit 118 is connected to a port 254 of block 252 via conductor 256. The computer 250 includes the capability for manually or otherwise inputting data that would affect the parameters, operation, or results achieved during an ablation procedure. A port 258 will provide, through conductor 260, an on/off switching function for RF generator 98. A reference voltage representative of a temperature can be applied to servo amplifier 94 through conductor 262 via port 264. The readout function formerly performed by readout 122 (see FIG. 5) can be provided by computer 250 by interconnecting conductor 266 via port 268. Furthermore, the curves displayed in FIGS. 7A and 7B may be readily displayed by computer 250 through use of its display screen 251.

With the use of a computer and associated software, it is now possible for a surgeon to determine on a real time basis the exact moment ablation occurs at an ablation site by denoting the presence of peak 200 (FIG. 7A) or peak 216 (FIG. 7B). Thereafter, further application of RF power is unnecessary and all of the potential hazards of overheating at the ablation site are avoided. However, as the depth of ablation in the tissue is or may be a function of the power level per time of applied RF power, radiation of RF energy may be continued until the level of ablation desired by the surgeon is achieved.

As discussed above, a catheter tip having multiple elements, as depicted in FIG. 6, can be used to simultaneously or sequentially ablate each of a plurality of sites. The use of a computer 250 permits real time monitoring of each ablation site. With such monitoring, control of RF power applied to each ablation site is readily available to a physician.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention.

What is claimed is:

1. Apparatus for sensing ablation of tissue at an ablation site during a tissue ablation procedure, said apparatus comprising in combination:

(a) a catheter having a tip for irradiating the ablation site with RF energy to perform the ablation procedure;

(b) a source of RF energy for transmitting RF energy to said tip;

(c) an electrode adapted to be adjacent tissue;

(d) a galvanic cell formed by said tip, said electrode and the tissue for generating a unique electrical signal responsive to ablation of the tissue at the ablation site; and (e) a control circuit responsive to the unique electrical signal for controlling the RF energy transmitted to said tip.

2. A method for sensing ablation of tissue at an ablation site during a tissue ablation procedure, said method comprising the steps of:

(a) transmitting RF energy to a tip from a source of RF energy;

(b) irradiating the ablation site with RF energy from the tip to perform the ablation procedure;

(c) locating an electrode adjacent tissue;

(d) generating an electrical signal responsive to ablation of the tissue at the ablation site with a galvanic cell formed by the tip, the electrode and the tissue; and (e) controlling the RF energy transmitted to the tip with a control circuit responsive to the electrical signal.

3. Apparatus for sensing ablation of tissue at an ablation site during a tissue ablation procedure, said apparatus comprising in combination:

(a) a catheter having a tip for irradiating the ablation site with RF energy to perform the ablation procedure;

(b) a source of RF energy for transmitting RF energy to said tip;

(c) an electrode adapted to be adjacent the tissue;

(d) a generator for generating an electrical signal responsive to ablation of the tissue at the ablation site, said generator comprising said tip, said electrode and the tissue; and (e) a control circuit for controlling the RF energy transmitted to said tip as a function of ablation of the tissue and in response to the electrical signal.

4. A method for sensing the occurrence of ablation of tissue at an ablation site during a tissue ablation procedure, said method comprising the steps of:

(a) transmitting RF energy from a source of RF energy to a tip;

(b) irradiating the ablation site with RF energy from the tip to perform the ablation procedure;

(c) locating an electrode adjacent the tissue;

(d) generating an electrical signal responsive to ablation of the tissue at the ablation site with a generator formed by the tip, the electrode and the tissue; and (e) controlling the RF energy transmitted to the tip with a control circuit as a function of the ablation of the tissue and responsive to the electrical signal.

5. Apparatus for sensing ablation of tissue at an ablation site during a tissue ablation procedure, said apparatus comprising in combination:

(a) a first electrode for irradiating the ablation site with RF energy to perform the ablation procedure;

(b) a source of RF energy for transmitting RF energy to said first electrode;

(c) a second electrode adapted to be adjacent tissue;

(d) a galvanic cell formed by said first and second electrodes and the tissue for generating a unique electrical signal responsive to ablation of the tissue at the ablation site; and (e) a control circuit responsive to the unique electrical signal for controlling the RF energy transmitted to said first electrode.

6. A method for sensing ablation of tissue at an ablation site during a tissue ablation procedure, said method comprising the steps of:

(a) transmitting RF energy from a source of RF energy to a first electrode;

(b) irradiating the ablation site with RF energy from the first electrode to perform the ablation procedure;

(c) locating a second electrode adjacent tissue;

(d) generating an electrical signal responsive to ablation of the tissue at the ablation site with a generator formed by the first and second electrodes and the tissue; and (e) controlling the RF energy transmitted to the first electrode with a control circuit responsive to the electrical signal.

7. Apparatus for sensing the extent of ablation of tissue at an ablation site during a tissue ablation procedure, said apparatus comprising in combination:

(a) a catheter having an electrode for irradiating the ablation site with RF energy to perform the ablation procedure;

(b) a source of RF energy for transmitting RF energy to said electrode;

(c) a further electrode adapted to be adjacent the tissue;

(d) a generator for generating an electrical signal responsive to ablation of the tissue at the ablation site, said generator comprising said electrode, said further electrode and the tissue; and (e) a control circuit for controlling the RF energy transmitted to said electrode as a function of ablation of the tissue and in response to the electrical signal.

8. A method for sensing the extent of ablation of tissue at an ablation site occurring during a tissue ablation procedure, said method comprising the steps of:

(a) transmitting RF energy from a source of RF energy to a first electrode;

(b) irradiating the ablation site with RF energy from the first electrode to perform the ablation procedure;

(c) locating a second electrode adjacent the tissue;

(d) generating an electrical signal responsive to ablation of the tissue at the ablation site with a generator comprising the first and second electrodes and the tissue; and (e) controlling the RF energy transmitted to the first electrode with a control circuit as a function of the ablation of the tissue and responsive to the electrical signal.

* * * * *